(12) United States Patent
Schmenger et al.

(10) Patent No.: US 7,465,322 B2
(45) Date of Patent: Dec. 16, 2008

(54) NACREOUS COLORANT FOR KERATIN FIBERS

(75) Inventors: Juergen Schmenger, Weiterstadt (DE); Jolanthe Kujawa, Darmstadt (DE)

(73) Assignee: Wella AG, Darmstadt (DE)

( * ) Notice: Subject to any disclaimer, the term of this patent is extended or adjusted under 35 U.S.C. 154(b) by 220 days.

(21) Appl. No.: 10/584,935

(22) PCT Filed: Oct. 19, 2004

(86) PCT No.: PCT/EP2004/011790

§ 371 (c)(1), (2), (4) Date: Jul. 3, 2006

(87) PCT Pub. No.: WO2005/074870

PCT Pub. Date: Aug. 18, 2005

(65) Prior Publication Data

US 2007/0151043 A1    Jul. 5, 2007

(30) Foreign Application Priority Data

Feb. 5, 2004   (DE) .................. 10 2004 005 768

(51) Int. Cl.
*A61Q 5/10* (2006.01)

(52) U.S. Cl. ............... 8/405; 8/406; 8/410; 8/435; 8/580; 8/611

(58) Field of Classification Search ........... 8/405, 8/406, 410, 435, 580, 611
See application file for complete search history.

(56) References Cited

U.S. PATENT DOCUMENTS

| 4,555,246 A | 11/1985 | Grollier et al. |
| 6,015,574 A * | 1/2000 | Cannell et al. ............ 424/450 |
| 6,372,203 B1 * | 4/2002 | Allwohn et al. .......... 424/70.13 |
| 6,528,045 B1 | 3/2003 | Golinski et al. |
| 6,562,772 B1 | 5/2003 | Maurin |
| 2002/0046432 A1 | 4/2002 | Laurent et al. |
| 2003/0135936 A1 | 7/2003 | Kleen et al. |
| 2004/0019982 A1 * | 2/2004 | Pratt et al. ..................... 8/405 |
| 2005/0081311 A1 | 4/2005 | Schmenger et al. |

FOREIGN PATENT DOCUMENTS

| DE | 38 34 142 | 4/1990 |
| DE | 3834142 | * 4/1990 |
| DE | 197 01 422 | 3/1998 |
| DE | 102 40 276 | 3/2004 |

OTHER PUBLICATIONS

English abstract of the Patent No. DE 3834142 A1 dated on 1990.*
Fiedler-Lexicon Der Hilfsstoffe, Band 1, 5-TH Auflage 2002, pp. 97-102.
E. Sagarin:"Cosmetics Scinece and Technology", Interscience Publishers Inc. MY 1958, pp. 503-507.
H. Janistyn: "Handbuch Der Kosmetika . . . " Band 3, 1973, pp. 388-397.
K. Schrader: "Grundlagen Und Rezepturen Der Kosmetika", 2. Auflage, 1989, pp. 787-815.

* cited by examiner

*Primary Examiner*—Eisa B Elhilo
(74) *Attorney, Agent, or Firm*—Michael J. Striker

(57) ABSTRACT

The dye carrier composition containing oxidative and/or non-oxidative dyes has a nacreous luster because it contains a combination of
(a) 6.1 to 20 weight percent of at least one fatty alcohol with 14 to 20 carbon atoms,
(b) 6.1 to 20 weight percent of at least one alkanolamide,
(c) 0.1 to 15 weight percent of at least one fatty alcohol alkoxylate or fatty acid alkoxylate and
(d) 0.1 to 15 weight percent of at least one anionic surfactant, wherein the weight ratio of fatty alcohol (a) to alkanolamide (b) is equal to 0.5:2 to 2:0.5, preferably from 0.8:1.2 to 1.2:0.8. The weight ratio of alkoxylate to anionic surfactant is preferably from 0.5:2 to 2:0.5.

13 Claims, No Drawings

NACREOUS COLORANT FOR KERATIN FIBERS

CROSS-REFERENCE

This is the US National Stage of PCT/EP 2004/011790, filed on Oct. 19, 2004 in Europe, which discloses the same invention as DE 10 2004 005768.0, filed Feb. 5, 2004 in Germany. The aforesaid German Patent Application provides the basis for a claim of priority for the invention described and claimed herein below under 35 U.S.C. 365 (b) and 35 U.S.C. 119 (a) to (d).

BACKGROUND OF THE INVENTION

The invention has for an object agents with a nacreous luster for coloring keratin fibers, particularly human hair, containing direct and/or oxidative dyes and a special combination of fatty alcohols, alkanolamides, alkoxylates and anionic surfactants, and the use of the aforesaid combination for producing a stable nacreous luster in hair colorants.

Coloring preparations are usually in the form of aqueous—preferably thickened—solutions or emulsions and besides dyes contain, for example, fatty alcohols and/or other oil components, emulsifiers, surfactants and optionally alcohols. Oxidation dyes as a rule consist of two components: (i) the dye carrier composition containing the dyes and (ii) the oxidant preparation, which are mixed with one another just before use and are then applied to the hair to be colored. If the coloring preparations are in the form of an emulsion, they are as a rule creams, but to obtain a nacreous luster effect it is necessary to add to them a special nacreous luster-imparting additive.

From DE-A 38 34 142 are known creamy hair colorants containing a multiplicity of raw materials including fatty alcohols and fatty alkanolamides as well as anionic and nonionic surfactants. These colorants, however, do not have a nacreous luster.

SUMMARY OF THE INVENTION

The purpose was therefore to develop a coloring composition which without the addition of a nacreous luster-imparting agent would by the selection of the raw materials alone have a stable nacreous character that would be retained even after the mixing with the oxidant preparation. Moreover, the hair-care effect after rinsing out the dye composition was to be improved over that of prior-art formulations.

We have now found that this objective can be reached in outstanding fashion by way of a combination of a fatty alcohol, alkanolamide, alkoxylate and anionic surfactant.

The object of the present invention is therefore a dye carrier composition containing oxidative and/or non-oxidative ("direct") dyes, characterized in that it contains a combination of
(a) 6.1 to 20 weight percent of at least one fatty alcohol with 14 to 20 carbon atoms,
(b) 6.1 to 20 weight percent of at least one alkanolamide,
(c) 0.1 to 15 weight percent of at least one fatty alcohol alkoxylate or fatty acid alkoxylate and
(d) 0.1 to 15 weight percent of at least one anionic surfactant, the weight ratio of fatty alcohol (a) to fatty alkanolamide (b) being 0.5:2 to 2:0.5.

DESCRIPTION OF THE PREFERRED EMBODIMENTS

Particularly preferred are dye carrier compositions wherein the fatty alcohol (a) and the alkanolamide (b) are present in a weight ratio from 0.8:1.2 to 1.2:0.8.

In addition, to obtain a particularly beautiful nacreous character and an unusually high hair-care effect after rinsing out the dye carrier, it is advantageous if the weight ratio of alkoxylate (c) to anionic surfactant (d) is equal to 0.5:2 to 2:0.5, a (c) to (d) weight ratio of 0.8:1.2 to 1.2:0.8 being particularly preferred.

Long-chain fatty alcohols with 14 to 20 carbon atoms suitable according to the invention are, for example, cetyl alcohol, stearyl alcohol, myristyl alcohol, isooctyl alcohol or isotridecyl alcohol. In the dye carrier composition of the invention, the fatty alcohols can be used alone or in combination with one another.

Alkanolamides suitable according to the invention are, in particular, the N-acyl derivatives of monoethanolamine or diethanolamine, for example the monoethanolamides or diethanolamides, or ester amides, such as coco fatty acid monoethanolamide.

Alkoxylates (c) suitable according to the invention are in particular ethoxylated fatty alcohols or fatty alcohol polyglycol ethers of the following formula:

$$CH_3(CH_2)x\text{-}O\text{---}(Ry)\text{-}H \quad (I)$$

[wherein $R=(CH_2\text{---}CH_2\text{---}O)$ or $(CH_3\text{---}CH\text{---}CH_2\text{---}O)$; $x=C_8\text{-}C_{18}$ and $y=2$ to 300]

Particularly preferred fatty alcohol alkoxylates are, for example, the polyethylene glycol ethers of stearyl alcohol, for example Steareth-10, Ceteareth-25 or Steareth-20.

According to the invention, suitable anionic surfactants are the salts and esters of carboxylic acids, alkyl ether sulfates and alkyl sulfates, fatty alcohol ether sulfates, sulfonic acids and salts thereof (sulfosuccinates, fatty acid isethionates etc), phosphate esters and salts thereof and acylamino acids and salts thereof.

A detailed description of these anionic surfactants can be found in the publication "FIEDLER—Lexikon der Hilfsfoffe" [FIEDLER—Encyclopedia of Auxiliary Substances], vol. 1, 5th edition (2002), pages 97 to 102, to which we hereby specifically refer.

The fatty alcohol of component (a) and the alkanolamide of component (b) are used in the dye carrier composition of the invention in a total amount from 7 to 12 weight percent each.

The alkoxylate of component (c) and the anionic surfactant of component (d) are preferably used in the dye carrier composition of the invention in a total amount from 7 to 12 weight percent each.

The dye carrier composition of the invention is preferably free of monomeric quaternary ammonium compounds and cationic emulsifiers and surfactants and optionally contains from 0.1 to 10 weight percent and preferably from 0.5 to 4 weight percent of ethylene glycol distearate.

The dye carrier composition of the invention preferably contains oxidation dye precursors from which the color is produced by action of an oxidant, for example hydrogen peroxide or an adduct thereof, or in the presence of atmospheric oxygen.

Suitable oxidation dye precursors are, for example the following developers and couplers and self-coupling compounds:
(i) Developers: 1,4-diaminobenzene (p-phenylenediamine), 1,4-diamino-2-methylbenzene (p-touylenediamine), 1,4-diamino-2,6-dimethylbenzene,1,4-diamino-3,5-diethylbenzene,1,4-diamino-mino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)-benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 2-[(2-acetylamino)ethoxy]-1,4-diaminobenzene, 4-phenylaminoaniline, 4-dimethylaminoaniline, 4-diethylaminoaniline, 4-dipropylaminoaniline, 4-[ethyl(2-hydroxyethyl)amino] aniline, 4-[di(2-hydroxy-ethyl)amino]aniline, 4-[di(2-hydroxyethyl)amino-2-methylaniline, 4-[(2-methoxyethyl) amino]aniline, 4-[(3-hydroxypropyl)amino]aniline, 4-[(2,3-dihydroxypropyl)amino]aniline, 1,4-diamino-2-(2-hydroxyethyl)benzene, 1,4-diamino-2-(1-methylethyl) benzene, 1,3-bis[(4-aminophenyl)(2-hydroxyethyl)-amino]-2-propanol, 1,4-bis[(4-aminophenyl)amino] butane, 1,8-bis(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)-phenol, 4-amino-2-fluorophenol, 4-amino-2-[(2-hydroxyethyl)amino]methylphenol, 4-amino-2-methylphenol, 4-amino-2-(methoxymethyl)phenol, 4amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol and 2-amino-5-meth-ylphenol, alone or in admixture with one another.

(ii) Couplers: N-(3-Dimethylaminophenyl)urea, 2,6-diaminopyridine, 2-amino-4-[(2-hydroxyethyl)amino]anisole, 2,4-diamino-1-fluoro-5-methylbenzene, 2,4amino-1-methoxy-5-methylbenzene, 2,4-diamino-1-ethoxy-5-methylbenzene, 2,4diamino-1-(2-hydroxyethoxy)-5-methyl-benzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxy-pyridine, 1,3-diaminobenzene, 2,4-diamino-1-(2-hydroxyethoxy)benzene, 1,3-diamino-4-(2,3-dihydroxypropoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxy-benzene, 2,6-bis(2-hydroxyethyl) aminotoluene, 4-hydroxyindole, 3-dimethylaminophenol, 3-dieth-ylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlo-rophenol, 3-amino-2-methylphenol, 3-amino-2-chloro-6-methylphenol, 3-aminophenol, 2-[(3-hydroxyphenyl)amino] acetamide, 5-[(2-hydroxyethyl)amino]-4-methoxy-2-methylphenol, 5-[(2-hydroxyethyl)amino]-2-methylphenol, 3[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 2-methyl-1-naphthol, 1,5-dihydroxynaphthalene, 1,7-dihydroxynaphthol, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione, alone or in admixture with one another.

(iii) Self-coupling compounds: 2-amino-5-methylphenol, 2-amino-6-methylphenol, 2-amino-5-ethoxyphenol or 2-propylamino-5-aminopyridine.

The total amount of oxidation precursors contained in the dye carrier composition of the invention is about 0.01 to 12 weight percent and particularly about 0.2 to 6 weight percent.

Moreover, to achieve certain color nuances the colorant can also contain common natural and/or synthetic direct dyes, for example vegetable dyes such as henna or indigo, triphenylmethane dyes, aromatic nitro dyes, azo dyes, quinone dyes or cationic or anionic dyes.

Suitable synthetic dyes are for example, the following: 1,4-bis[(2-hydroxyethyl)amino]-2-nitrobenzene, 1-(2-hydroxyethyl)amino-2-nitro-4-[di(2-hydroxyethyl)amino]benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[(2,3-di-hydroxypropyl) amino]-4[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl)amino]-2-nitrobenzene (HC Blue No. 6), 2-[(4-amino-2-nitrophenyl) amino]-5-dimethylaminobenzoic acid (HC Blue No. 13), 1-amino-4-[(2-hydroxyethyl)amino]-2-nitrobenzene (HC Red No. 7), 2-amino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-3-nitrophenol, 4-[(2-hydroxyethyl)-amino]-3-nitrophenol, 1-[(2-aminoethyl) amino]-4-(2-hydroxyethoxy)-2-nitrobenzene (HC Orange No. 2), 4-(2,3-dihydroxypropoxy)-1-[(2-hydroxyethyl) amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl) amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino]benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzoxazine, (HC Red. No. 14), 1-amino-2-[(2-hydroxy-ethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)-amino]-5-nitrophenol (HC Yellow No. 11), 3-[(2-aminoethyl)amino]-1-methoxy-4-nitro-benzene hydrochloride (HC Yellow No. 9), 1-[(2-ureidoethyl)amino]-4-nitrobenzene, 4-[(2,3-dihydroxypropyl)amino]-3-nitro-1-trifluoromethylbenzene (HC Yellow No. 6), 1-chloro-2,4-bis[(2-hydroxyethyl)amino]-5-nitrobenzene (HC Yellow No. 10), 4[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 1,4-di[(2,3-dihydroxypropyl)amino]-9,10-anthraquinone, 1-[(2-hydroxyethyl)amino]-4-methylamino-9,10-anthraquinone (CI 61505, Disperse Blue No. 3), 2-[(2-aminoethyl)amino]-9,10-anthraquinone (HC Orange No. 5), 1-hydroxy-4-[(4-methyl-2-sulfophenyl)amino]-9,10-anthraquinone, 1-[(3-aminopropyl)amino]-4-methylamino-9,10-anthraquinone (HC Blue No. 8), 1-[(3-aminopropyl)-amino]-9, 10-anthraquinone (HC Red No. 8), 1,4-diamino-2-methoxy-9, 1 0-anthraquinone (CI 62015, Disperse Red No. 11, Solvent Violet No. 26), 1,4-dihydroxy-5,8-bis[2-hydroxyethyl)amino]-9,10-anthraquinone (CI 62500, Disperse Blue No. 7, Solvent Blue No. 69), 9-(dimethylamino)-benzo[a]-phenoxazin-7-ium chloride (CI 51175; Basic Blue No. 6), di[4-(diethylamino) phenyl][4-(ethylamino)naphthyl]carbenium chloride (CI 42595; Basic Blue No. 7), 3,7-di(dimethyl-amino)phenothiazin-5-ium chloride (CI 52015; Basic Blue No. 9), di[4-(dimethylamino)phenyl][4-(phenylamino)naphthyl]carbenium chloride (CI 44045; Basic Blue No. 26), 2-{[4-(ethyl(2-hydro-xyethyl)amino)phenyl]azo}-6-methoxy-3-methylbenzothiazolium methylsulfate (CI 11154; Basic Blue No. 41), 8-amino-2-bromo-5-hydroxy-4-imino-6-{[3-(trimethylammonio)phenyl]amino}-1(4H-naphthalenone chloride (CI 56059; Basic Blue No. 99), bis[4-(dimethyl-amino)phenyl][4-(methylamino)phenyl]carbenium chloride (CI 42535; Basic Violet No. 1), tris[4-(dimethyl-amino)phenyl]carbenium chloride (CI 42555; Basic Violet No. 3), 2-[3,6-(diethylamino)-dibenzopyranium-9-yl]benzoyl chloride (CI 45170; Basic Violet No. 10), di(4-aminophenyl)(4-amino-3-methylphenyl)carbenium chloride (CI 42510, Basic Violet No. 14), 1,3-bis[(2,4-dia-mino-5-methylphenyl)azo]-3-methylbenzene (CI 21010; Basic Brown No. 4), 1-[(4-aminophenyl) azo]-7-(trimethylammonio)-2-naphthol chloride (CI 12250; Basic Brown No. 16), 1-[(4-amino-2-nitrophenyl)azo]-7-(trimethylammonio-2-naphthol chloride (Basic Brown No. 17), 1-[(4-amino-3-nitrophenyl)azo]-7-(trimethylammonio)-2-naphthol chloride (CI 12251; Basic Brown No. 17 [sic]), 3,7-diamino-2,8-dimethyl-5-phenylphenazinium chloride (CI 50240; Basic Red No. 2), 1,4-dimethyl-5-{[(4-(dimethyl-lamino)phenyl]azo}-1,2,4-triazolium chloride (CI 11055; Basic Red No. 22), 2-hydroxy-1-[(2-methoxyphenyl)azo]-7-(trimethylammonio)naphthalene chloride (CI 12245; Basic Red No. 76), 2-{2-[(2,4-dimethoxyphenyl)amino]ethenyl}-1,3,3-trimethyl-3H-indol-1-ium chloride (CI 48055; Basic Yellow No. 11), 3-methyl-1-phenyl-4-{[3-(trimethylammonio)phenyl]azo}pyrazol-5-one chloride (CI 12719; Basic Yellow No. 57), bis[4-(diethylamino)phenyl]phenylcarbenium hydrogen sulfate (1:1) (CI 42040; Basic Green No. 1), 1-[di(2-hydroxyethyl)amino]-3-methyl-4-[(4-nitrophenyl) azo]benzene (CI 11210; Disperse Red No. 17), 4-[(4-aminophenyl)azo]-1-[di(2-hydroxyethyl)amino]-3-methylbenzene (HC Yellow No. 7), 2,6-diamino-3-[(pyridin-3-yl)-azo] pyridine, 6-hydroxy-5-[(4-sulfophenyl)azo] naphthalenesulfonic acid disodium salt (CI 15985; Food Yellow No. 3; FD&C Yellow No. 6), 2,4-dinitro-1-naphthol-7-sulfonic acid disodium salt (CI 10316; Acid Yellow No. 1; Food Yellow No. 1), 2-(indan-1,3-dion-2-yl)-quinoline-x,x-sulfonic acid (mixture of mono- and disulfonic acid) (CI 47005; D&C Yellow No. 10; Food Yellow No. 13; Acid Yellow No. 3), 5-hydroxy-1-(4-sulfophenyl)-4-[(4-sulfophenyl) azo]pyrazole-3-carboxylic acid trisodium salt (CI 19140; Food Yellow No. 4; Acid Yellow No. 23), 9-(2-carboxyphenyl)-6-hydroxy-3H-xanthen-3-one (CI 45350; Acid Yellow No. 73; D&C Yellow No. 8), 5-[(2,4-dinit-rophenyl)amino]-2-phenylaminobenzenesulfonic acid sodium salt (CI 10385; Acid Orange No. 3), 4-[(2,4-dihydroxyphenyl)azo]benzenesulfonic acid monosodium salt (CI 14270; Acid Orange No. 6), 4-[(2-hydroxynaphth-1-yl)azo]benzenesulfonic acid sodium salt (CI 15510; Acid Orange No. 7), 4-[(2,4-dihydroxy-3-[(2,4-dimethylphenyl)azo]phenyl]azo]benzene-sulfonic acid sodium salt (CI 20170; Acid Orange No. 24), 4-hydroxy-3-[(4-sulfonaphth-1-yl)azo]-1-naphthalene-sulfonic acid disodium salt (CI 14720; Acid Red No. 14), 6-hydroxy-5-[(4-sulfonaphth-1-yl)azo]-2,4-naphthalenedisulfonic acid trisodium salt (CI 16255; Ponceau 4R; Acid Red No. 18), 3-hydroxy-4-[(4-sulfonaphth-1-yl)azo]-2,7-naphthalenedisulfonic acid trisodium salt (CI 16185; Acid Red No. 27), 8-amino-1-hydroxy-2-(phenylazo)-3,6-naphthalenedisulfonic acid disodium salt (CI 17200; Acid Red No. 33), 5-(acetylamino)-4-hydroxy-3-[(2-methylphenyl)azo]-2,7-naphthalenedisulfonic acid disodium salt (CI 18065; Acid Red No. 35), 2-(3-hydroxy-2,4,5,7-tetraiododibenzopyran-6-n-9-yl)benzoic acid disodium salt (CI 45430; Acid Red No. 51), N-[6-(diethylamino)-9-(2,4-disulfophenyl)-3H-xanthen-3-ylidene]-N-ethylethanammonium hydroxide, inner salt, sodium salt (CI 45100; Acid Red No. 52), 8-{[4(phenylazo)phenyl]azo}-7-naphthol-1,3-disulfonic acid disodium salt (CI 27290; Acid Red No. 73), 2',4',5',7'-tetrabromo-3', 6'-dihydroxyspiro{isobenzofuran-1 (3H),9'-[9H]-xanthen}-3-one disodium salt (CI 45380; Acid Red No. 87), 2', 4', 5', 7'-tetrabromo-4,5,6,7-tetrachloro-3', 6'-dihydroxyspiro{isobenzofuran-1(3H),9'-[9H]-xanthen}-3-one disodium salt (CI 45410; Acid Red No. 92), 3', 6'-dihydroxy-4', 5'-diiodospiro{isobenzofuran-1(3H),9'-(9H) xanthen}-3-one disodium salt (CI 45425; Acid Red No. 95), (2-sulfophenyl)di[4(ethyl-((4sulfophenyl)methyl)amino) phenyl]-carbenium disodium salt betaine (CI 42090; Acid Blue No. 9; FD&C Blue No. 1), 1,4-bis[(2-sulfo-4-methylphenyl)amino]-9,10-anthraquinone disodium salt (CI 61570; Acid Green No. 25), bis[4-(dimethylamino)phenyl]-(3,7-disulfo-2-hydroxynaphth-1-yl)carbenium inner salt, monosodium salt (CI 44090; Food Green No. 4; Acid Green No. 50), bis[4-(di-ethylamino)phenyl](2,4disulfophenyl)carbenium inner salt, sodium salt (2:1) (CI 42045; Food Blue No. 3; Acid Blue No. 1), bis[4-(diethylamino)phenyl](5-hydroxy-2,4-disulfophenyl)carbenium inner salt, calcium salt (2:1) (CI 42051; Acid Blue No. 3), 1-amino-4-(cyclohexylamino)-9,10-anthraquinone-2-sulfonic acid sodium salt (CI 62045; Acid Blue No. 62), 2-(1,3-dihydro-3-keto-5-sulfo-2H-indol-2-ylidene)-2,3-dihydro-3-keto-1H-indole-5-sulfonic acid disodium salt (CI 73015; Acid Blue No. 74), 9-(2-carboxyphenyl)-3-[(2-methylphenyl)amino]-6-[(2-methyl-4-sulfophenyl)amino]xanthylium inner salt, monosodium salt (CI 45190; Acid Violet No. 9), 1-hydroxy-4-[(4-methyl-2-sulfophenyl)amino]-9,10-anthraquinone sodium salt (CI 60730; D&C Violet No. 2; Acid Violet No. 43), bis{3-nitro-4-[(4-phenylamino)-3-sulfophenylamino]phenyl} sulfone (CI 10410; Acid Brown No. 13), 5-amino-4-hydroxy-6-[(4nitrophenyl)azo]-3-(phenylazo)-2,7-naphthalenedisulfonic acid disodium salt (CI 20470; Acid Black No. 1), 3-hydroxy-4-[(2-hydroxynaphth-1-yl)azo]-7-nitro-1-naphthalenesulfonic acid chromium complex (3:2) (CI 15711; Acid Black No. 52), 3-[(2,4dimethyl-5-sulfophenyl)azo]-4-hydroxy-1-naphthalenesulfonic acid disodium salt (CI 14700; Food Red No. 1; FD&C Red No. 4), 4-(acetylamino)-5-hydroxy-6-[(7-sulfo-4-[(4-sulfophenyl)azo]naphth-1-yl)azo]-1,7-naphthalene-disulfonic acid tetrasodium salt (CI 28440; Food Black No. 1) and 3-hydroxy-4(3-methyl-5-keto-1-phenyl-4,5-dihydro-1H-pyrazol-4-ylazo)naphthalene-1-sulfonic acid sodium salt, chromium complex (Acid Red No. 195), alone or in combination with one another The total amount of direct dyes in the dye carrier composition of the invention is about 0.01 to 7 weight percent and preferably about 0.2 to 4 weight percent.

Other common dyes known to be used for hair coloring and that can be contained in the colorant of the invention are described in, among other publications, E. Sagarin, "Cosmetics, Science and Technology", Interscience Publishers Inc., New York (1957), pages 503 ff, in H. Janistyn, "Handbuch der Kosmetika und Riechstoffe" [Handbook of Cosmetics and Fragrances], vol. 3 (1973), pages 388 ff. and in K. Schrader "Grundlagen und Rezepturen der Kosmetika" [Fundamentals and Formulations of Cosmetics], 2nd edition, (1989), pages 782 to 815, to which we hereby specifically refer.

Although oxidation colorants are preferred, the dye carrier composition of the invention can, of course, also be in the form of a nonoxidative colorant based on the afore-said direct dyes. Furthermore, the dye carrier composition of the invention can contain antioxidants, for example ascorbic acid, thioglycolic acid or sodium sulfite, as well as complexing agents for heavy metals, for example an ethylenediaminetetraacete or nitriloacetic acid, in an amount of up to about 0.5 weight percent. Perfume oils can be contained in the dye carrier composition of the invention in an amount of up to about 1 weight percent. Naturally, the afore-described dye carrier composition can optionally also contain other additives commonly used in hair colorants, for example thickeners such as, for example, the homopolymers of acrylic acid, vegetable gums, derivatives of cellulose and starch, algal polysaccharides, amphiphilic associative thickeners, moreover preservatives, antioxidants, for example sodium sulfite, thioglycolic acid and ascorbic acid, complexing agents, solvents such as water, lower aliphatic alcohols, for example aliphatic alcohols with 1 to 4 carbon atoms such as ethanol, propanol and isopropanol, or glycols such as glycerol and 1,2-propylene glycol, wetting agents or emulsifiers from the classes of anionic, amphoteric or nonionic surfactants not mentioned in the main claims, moreover softeners, vaseline, silicone oils, paraffin oil, polysorbates and fatty acids as well as hair-care agents such as cationic polymers or resins, lanolin derivatives, cholesterol, vitamins, pantothenic acid and betaine. The said constituents are used in amounts normally employed for such purposes, for example the wetting agents and emulsifiers at a concentration of 0.1 to 30 weight percent and the hair-care agents at a concentration of 0.1 to 5.0 weight percent.

For nonoxidative colorants based on direct dyes, the pH of the dye carrier composition of the invention is in the range from about 5 to 10 and preferably from 6 to 9, whereas for oxidative colorants based on oxidation dye precursors the pH is in the range from about 6 to 12 and preferably from 9 to 11. The pH of the ready-to-use oxidation hair colorant (namely the mixture of the dye carrier composition of the invention and the oxidant) is about 5.5 to 10 and preferably 6 to 9.

Depending on the composition and the desired pH, the pH is preferably adjusted with ammonia or an organic amine, for example a glucamine, aminomethylpropanol, monoethanolamine or triethanolamine, an inorganic base, for example sodium hydroxide, potassium hydroxide, sodium carbonate or calcium hydroxide, or with an organic or inorganic acid, for example lactic acid, citric acid, acetic acid or phosphoric acid.

The dye carrier composition of the invention is preferably packaged in the form of an aqueous or aqueous-alcoholic preparation, for example as a thickened solution, emulsion, cream or gel.

For oxidative coloring, the afore-described dye carrier composition is mixed with an oxidant just before use, and an amount of the ready-to-use preparation sufficient for the coloring, as a rule about 60 to 200 grams, is applied to the fibers.

If the dye carrier composition of the invention contains no oxidation dye precursors or contains oxidation dye precursors that are readily oxidized by atmospheric oxygen, it can be applied to the keratin fibers directly without previous mixing with an oxidant.

Suitable oxidants for developing the coloration are mainly hydrogen peroxide or the addition compounds thereof to urea, melamine or sodium borate in the form of a 1 to 12 percent, preferably 1.5 to 6 percent aqueous solution. The mixing ratio of dye carrier composition to oxidant depends on the concentration of the oxidant and as a rule is about 5:1 to 1:2 and preferably 1:1, the oxidant being contained in the ready-to-use preparation preferably in an amount from about 0.5 to 8 weight percent and particularly from 1 to 4 weight percent.

The ready-to-use colorant is allowed to act on the keratin fibers (for example on human hair) at 15 to 50° C. for about 10 to 45 minutes and preferably for about 15 to 30 minutes after which the fibers are rinsed with water. Optionally, following this rinsing the fibers are washed with a shampoo and possibly post-rinsed with a weak organic acid, for example tartaric acid. The keratin fibers are then dried.

The dye carrier composition of the invention has a uniform consistency and produces a highly cosmetic, nacreous luster effect. A colorant prepared with the dye carrier composition of the invention meets the requirements in terms of adhesion properties, application performance and viscosity adjustment in outstanding manner and through the nacreous character provides a highly cosmetic appearance. In addition, compared to the known colorants, it gives a clearly improved hair-care effect after rinsing.

Another object of the present application is the use of a combination of (a) at least one fatty alcohol with 14 to 20 carbon atoms, (b) at least one alkanolamide, (c) at least one fatty alcohol alkoxylate or fatty acid alkoxylate and (d) at least one anionic surfactant, the weight ratio of fatty alcohol (a) to alkanolamide (b) being equal to 0.5:2 to 2:0.5, for producing a nacreous luster effect in dye carrier compositions and colorants for keratin fibers, particularly human hair.

Particularly preferred is the use of a combination of (a) 6.1 to 20 weight percent, particularly 7 to 12 weight percent, of at least one fatty alcohol with 14 to 20 carbon atoms, (b) 6.1 to 20 weight percent and particularly 7 to 12 weight percent of at least one alkanolamide, (c) 0.1 to 15 weight percent and particularly 7 to 12 weight percent of at least one fatty alcohol alkoxylate or fatty acid alkoxylate, and (d) 0.1 to 15 weight percent and particularly 7 to 12 weight percent, of at least one anionic surfactant, the weight ratio of fatty alcohol (a) to alkanolamide (b) being equal to 0.5:2 to 2:0.5 and particularly 0.8:1.2 to 1.2:0.8.

The following examples will explain the subject matter of the invention in greater detail without limiting it to the examples.

EXAMPLES

Example 1

Oxidation Hair Colorant, Creamy

| | | |
|---|---|---|
| 6.0000 | g | of stearyl alcohol |
| 5.0000 | g | of cetyl alcohol |
| 8.0000 | g | of coco fatty acid monoethanolamide (Cocamide MEA) |
| 4.0000 | g | of polyoxyethylene(10) stearyl ether (Steareth-10) |
| 8.0000 | g | of sodium lauryl alcohol diethylene glycol ether sulfate, 28% aqueous solution |
| 1.3620 | g | of 4-aminophenol |
| 0.5000 | g | of 1-naphthol |
| 0.0136 | g | of resorcinol |
| 0.0034 | g | of 2-amino-6-chloro-4-nitrophenol |
| 12.0000 | g | of ammonia, 25% aqueous solution |
| 1.0000 | g | of disodium ethylenediaminetetraacetate |
| 1.0000 | g | of ascorbic acid |
| to 100.0000 | g | water |

Just before use, 50 g of the foregoing dye carrier composition with a nacreous luster was mixed with 50 g of a 6% aqueous hydrogen peroxide solution. This gave a homogeneous, cosmetically attractive colorant preparation with a nacreous luster. The mixture thus obtained was then applied to natural blond hair. After an exposure time of 30 minutes at 40° C., the hair was rinsed with water and dried. The hair had a bright copper-red color.

Example 2

Oxidation Hair Colorant for Color-Brightening

Component (A): Creamy Dye Carrier Composition

| | | |
|---|---|---|
| 12.00 | g | of cetylstearyl alcohol |
| 8.00 | g | of coco fatty acid monoethanolamide (Cocamide MEA) |
| 6.00 | g | of polyoxyethylene(25) cetylstearyl ether (Ceteareth-25) |
| 1.00 | g | of oleic acid |
| 4.00 | g | of sodium lauryl alcohol diethylene glycol ether sulfate, 70% aqueous solution |
| 0.50 | g | of p-phenylenediamine |
| 0.07 | g | of resorcinol |
| 1.00 | g | of disodium ethylenediaminetetraacetate |
| 8.00 | g | of ammonia, 25% aqueous solution |
| 8.00 | g | of ethanol |
| to 100.00 | g | water |

Component B: Hydrogen Peroxide Emulsion

| | | |
|---|---|---|
| 10.0 | g | of cetylstearyl alcohol |
| 1.5 | g | of cholesterol |
| 4.0 | g | of sodium lauryl alcohol diethylene glycol ether sulfate, 28% aqueous solution |
| 35.0 | g | of hydrogen peroxide, 35% aqueous solution |
| 0.3 | g | of perfume |
| to 100.0 | g | water |

Just before use, 40 g of the liquid dye carrier composition (A) with a nacreous luster was mixed with 80 g of the hydrogen peroxide emulsion (B) which corresponded to an (A):(B) mixing ratio of 1:2, and 120 g of this mixture was applied to gray human hair. After an exposure time of 20 minutes at room temperature, the hair was rinsed with water and dried. The hair treated in this manner had a uniform light-brown color from the roots to the tips. The ready-to-use agent had a cosmetic nacreous luster, was easy to apply to the hair and did not run off the hair.

Example 3

Oxidation Hair Colorant, Creamy

| | | |
|---|---|---|
| 4.00 | g | of cetylstearyl alcohol |
| 5.00 | g | of stearyl alcohol |
| 12.00 | g | of coco fatty acid monoethanolamide (Cocamide MEA) |
| 2.00 | g | of polyoxyethylene(20) stearyl ether (Steareth-20) |
| 8.00 | g | of sodium lauryl alcohol diethylene glycol ether sulfate, 28% aqueous solution |
| 8.00 | g | of monoethanolamine |
| 1.30 | g | of 1-methyl-2,5-diaminobenzene |
| 1.50 | g | of diallyldiammonium chloride/hydroxyethylcellulose copolymer (Polyquaternium-4) |
| 0.65 | g | of resorcinol |
| 0.50 | g | of keratin hydrolyzate |
| 0.50 | g | of silk protein hydrolyzate |
| 0.52 | g | of 2-amino-6-chloro-4-nitrophenol |
| 1.00 | g | of disodium ethylenediaminetetraacetate |
| 0.30 | g | of ascorbic acid |
| to 100.00 | g | water |

Just before use, 50 g of the foregoing dye carrier composition with a nacreous luster was mixed with 50 g of a 12% aqueous hydrogen peroxide solution. The resulting mixture was then applied to natural blond hair. After an exposure time of 30 minutes at 40° C., the hair was rinsed with water and dried. This gave a uniform, strong brown shade.

Example 4

Nonoxidative Hair Colorant

| | | |
|---|---|---|
| 6.000 | g | of stearyl alcohol |
| 4.000 | g | of myristyl alcohol |
| 8.000 | g | of coco fatty acid monoethanolamide (Cocamide MEA) |
| 2.000 | g | of polyoxyethylene(20) stearyl ether (Steareth-20) |
| 2.000 | g | of sodium lauryl sulfate |
| 2.000 | g | of isopropyl alcohol |
| 0.160 | g | of {{4-{ethyl[(2-hydroxyethyl)amino]-2-nitrophenyl}amino}}ethanol hydrochloride (HC Blue No. 12) |
| 0.170 | g | of 3-{[2-nitro-4-(trifluoromethyl)phenyl]amino}-1,2-propanediol (HC Yellow No. 6) |
| 0.012 | g | of 1-N-hydroxyethylamino-4-methyl-2-nitrobenzene |
| 0.035 | g | of HC RED NO. 10 and HC RED NO. 11 (1:1) |
| to 100.000 | g | water |

The creamy dye carrier composition with a nacreous luster was applied with gloves to washed and towel-dried, natural blond hair. After an exposure time of 20 to 25 minutes, excess dye was washed out with water and a shampoo. This gave a beautiful, lustrous medium-blond shade.

Example 5

Nonoxidative Hair Colorant

| | |
|---|---|
| 3.1 g | of cetylstearyl alcohol |
| 3.1 g | of stearyl alcohol |
| 5.0 g | of coco fatty acid diethanolamide (Cocamide DEA) |
| 2.0 g | of polyoxyethylene(30) oleyl ether (Oleth-30) |
| 0.5 g | of sodium lauryl sulfate |
| 7.0 g | of ethanol |
| 0.1 g | of 1-N-hydroxyethylamino-4-methyl-2-nitrobenzene |
| 0.5 g | of HC RED NO. 10 and HC RED NO. 11 (1:1) |
| 0.2 g | of 2-amino-6-chloro-4-nitrophenol |
| to 100.0 g | water |

The creamy dye carrier composition with a nacreous luster was applied with gloves to washed and towel-dried, natural blond hair. After an exposure time of 25 to 30 minutes, excess dye was washed out with water and a shampoo. This gave a lustrous trendy red shade.

Unless otherwise indicated, all percentages given in the present application are by weight.

The invention claimed is:

1. A dye carrier composition with a nacreous luster, said dye carrier composition containing oxidative dyes and/or nonoxidative dyes, and a combination of:
   (a) from 6.1 to 20 weight percent of at least one fatty alcohol with 14 to 20 carbon atoms,
   (b) from 6.1 to 20 weight percent of at least one alkanolamide,
   (c) from 0.1 to 15 weight percent of at least one fatty alcohol alkoxylate or fatty acid alkoxylate, and
   (d) from 0.1 to 15 weight percent of at least one anionic surfactant; wherein a weight ratio of said fatty alcohol to said alkanolamide is from 0.5:2 to 2:0.5.

2. The dye carrier composition as defined in claim 1, wherein said weight ratio of said fatty alcohol to said alkanolamide is from 0.8:1.2 to 1.2:0.8.

3. The dye carrier composition as defined in claim 1, wherein a weight ratio of said alkoxylate to said anionic surfactant is from 0.5:2 to 2:0.5.

4. The dye carrier composition as defined in claim 1, wherein said fatty alcohol is selected from the group consisting of cetyl alcohol, stearyl alcohol, myristyl alcohol, isooctyl alcohol, isotridecyl alcohol and mixtures thereof.

5. The dye carrier composition as defined in claim 1, wherein said at least one alkanolamide is selected from the group consisting of N-acyl derivatives of monoethanolamine and N-acyl derivatives of diethanolamine.

6. The dye carrier composition as defined in claim 1, wherein said alkoxylate consists of at least one ethoxylated fatty alcohol of formula (I):

$$CH_3(CH_2)\text{—}X\text{—}O\text{—}(R_y)\text{—}H \qquad (I),$$

wherein R=—(CH2—CH2—O)— or —(CH3—CH—CH2—O)—, and X represents $C_8$-$C_{18}$ and y denotes 2 to 300.

7. The dye carrier composition as defined in claim 1, wherein said at least one anionic surfactant is selected from the group consisting of carboxylic acid salts, carboxylic acid esters, alkyl ether sulfates, alkyl sulfates, fatty alcohol ether sulfates, sulfonic acids, salts of sulfonic acids, phosphate esters, phosphate salts, acylamino acids and salts of acylamino acids.

8. The dye carrier composition as defined in claims 1, containing a total amount of from 7 to 12 weight percent of each of said fatty alcohol, said alkanolamide, said alkoxylate, and said anionic surfactant.

9. The dye carrier composition as defined in claim 1, and free of monomeric quaternary ammonium compounds and free of cationic emulsifiers and surfactants.

10. The dye carrier composition as defined in claims 1, containing from 0.1 to 10 weight percent of ethylene glycol distearate.

11. An agent for oxidative coloring of hair obtained by mixing a dye carrier composition with an oxidant;
   wherein said dye carrier composition contains oxidative dyes and/or nonoxidative dyes, and a combination of:
   (a) from 6.1 to 20 weight percent of at least one fatty alcohol with 14 to 20 carbon atoms,
   (b) from 6.1 to 20 weight percent of at least one alkanolamide,
   (c) from 0.1 to 15 weight percent of at least one fatty alcohol alkoxylate or fatty acid alkoxylate, and
   (d) from 0.1 to 15 weight percent of at least one anionic surfactant; wherein a weight ratio of said fatty alcohol to said alkanolamide is from 0.5:2 to 2:0.5.

12. The agent as defined in claim 11, wherein said oxidant is hydrogen peroxide.

13. A method of making a dye carrier composition or a colorant for keratin fibers with a nacreous luster, said method comprising the step of including in said dye carrier composition a combination of:
   (a) from 6.1 to 20 weight percent of at least one fatty alcohol with 14 to 20 carbon atoms,
   (b) from 6.1 to 20 weight percent of at least one alkanolamide,
   (c) from 0.1 to 15 weight percent of at least one fatty alcohol alkoxylate or fatty acid alkoxylate, and
   (d) from 0.1 to 15 weight percent of at least one anionic surfactant; wherein a weight ratio of said at least one fatty alcohol to said at least one alkanolamide (b) is from 0.5:2 to 2:0.5.

* * * * *